United States Patent
Ono et al.

(10) Patent No.: US 10,508,068 B2
(45) Date of Patent: Dec. 17, 2019

(54) PRODUCTION METHOD FOR INCLUSION COMPOUND

(71) Applicant: NIPPON SODA CO., LTD., Tokyo (JP)

(72) Inventors: Kazuo Ono, Ichihara (JP); Eiji Hoshi, Ichihara (JP)

(73) Assignee: NIPPON SODA CO., LTD., Tokyo (JP)

(*) Notice: Subject to any disclaimer, the term of this patent is extended or adjusted under 35 U.S.C. 154(b) by 0 days.

(21) Appl. No.: 15/540,135

(22) PCT Filed: Jan. 13, 2016

(86) PCT No.: PCT/JP2016/000128
§ 371 (c)(1),
(2) Date: Jun. 27, 2017

(87) PCT Pub. No.: WO2016/117295
PCT Pub. Date: Jul. 28, 2016

(65) Prior Publication Data
US 2018/0022675 A1    Jan. 25, 2018

(30) Foreign Application Priority Data
Jan. 19, 2015  (JP) .............................. 2015-007987

(51) Int. Cl.
| | | |
|---|---|---|
| C07C 65/03 | (2006.01) | |
| C07C 37/00 | (2006.01) | |
| C07C 39/15 | (2006.01) | |
| C07D 233/58 | (2006.01) | |
| C07D 233/64 | (2006.01) | |
| C08G 59/56 | (2006.01) | |
| C08G 59/62 | (2006.01) | |
| C08G 59/50 | (2006.01) | |
| C08G 59/42 | (2006.01) | |

(52) U.S. Cl.
CPC .............. *C07C 39/15* (2013.01); *C07C 37/00* (2013.01); *C07C 65/03* (2013.01); *C07D 233/58* (2013.01); *C07D 233/64* (2013.01); *C08G 59/4223* (2013.01); *C08G 59/5073* (2013.01); *C08G 59/56* (2013.01); *C08G 59/621* (2013.01)

(58) Field of Classification Search
CPC ......... C07C 65/03; C07C 37/00; C07C 39/15; C07D 233/58; C07D 233/64; C08G 59/56
See application file for complete search history.

(56) References Cited

U.S. PATENT DOCUMENTS

| | | | |
|---|---|---|---|
| 8,623,942 B2* | 1/2014 | Kaneko .............. | C08G 59/5073 523/455 |
| 2010/0022744 A1 | 1/2010 | Kaneko et al. | |
| 2010/0179250 A1 | 7/2010 | Ono et al. | |
| 2012/0004349 A1 | 1/2012 | Kaneko et al. | |
| 2012/0004377 A1 | 1/2012 | Kaneko et al. | |
| 2012/0088920 A1 | 4/2012 | Kaneko et al. | |

FOREIGN PATENT DOCUMENTS

| | | |
|---|---|---|
| CN | 101802049 A | 8/2010 |
| JP | 2007-039449 A | 2/2007 |
| JP | 2007-191450 A | 8/2007 |
| JP | 2010-180337 A | 8/2010 |
| JP | 2012-232994 A | 11/2012 |
| JP | 2013-213168 A | 10/2013 |
| TW | 201037007 A | 10/2010 |
| TW | 201037008 A | 10/2010 |
| WO | 2008/075427 A1 | 6/2008 |
| WO | 2010/103809 A1 | 9/2010 |

OTHER PUBLICATIONS

Machine translation of CN101802049, 2010.*
Takeda et al., "Structure comparison of inclusion crystals of 1,1,2,2-tetrakis (4-hydroxyphenyl)ethane and imidazole derivatives, and guest release behavior," The 89th Annual Meeting of the Chemical Society of Japan in Spring vol. 89, 3 B4-13, 2009.
Jul. 25, 2017 International Preliminary Report on Patentability issued in International Patent Application No. PCT/JP2016/000128.
Feb. 23, 2016 International Search Report issued in International Application No. PCT/JP2016/000128.
Jul. 16, 2018 Extended European Search Report issued in European Patent Application No. 16739906.2.

* cited by examiner

*Primary Examiner* — Sun Jae Yoo
(74) *Attorney, Agent, or Firm* — Oliff PLC

(57) ABSTRACT

A method for producing a thermodynamically more stable clathrate compound including at least one compound selected from the group consisting of 1,1,2,2-tetrakis(4-hydroxyphenyl)ethane, 5-hydroxyisophthalic acid, and 5-nitroisophthalic acid as a host compound and an imidazole compound as a guest compound. The method for producing a clathrate compound includes: a mixing step of mixing a mixed solvent including a protic solvent, at least one compound selected from the group consisting of 1,1,2,2-tetrakis (4-hydroxyphenyl)ethane, 5-hydroxyisophthalic acid and 5-nitroisophthalic acid, and an imidazole compound; and a heating step.

2 Claims, No Drawings

PRODUCTION METHOD FOR INCLUSION COMPOUND

TECHNICAL FIELD

The present invention relates to a novel method for producing a clathrate compound.

The present application claims priority to Japanese Patent Application No. 2015-7987 filed on Jan. 19, 2015, the contents of which are incorporated herein by reference.

BACKGROUND ART

An imidazole compound is widely used as a raw material for a medicine and a pesticide, a metal surface treatment agent, or a curing agent or a curing accelerator for epoxy resin.

When an imidazole compound is used as a curing agent or a curing accelerator for epoxy resin, there is an advantage that the epoxy resin may be cured in a short time at a low temperature, and that the mechanical properties, electrical properties, and the like of the cured product are satisfactory. On the other hand, there has been a problem that the curing reaction starts at room temperature, reducing storage stability. Therefore, there has been an attempt to give latency to an imidazole compound by forming a clathrate compound of the imidazole compound, and the following methods are known as a method for producing a clathrate compound comprising an imidazole compound.

Patent Document 1 describes that, as a method for producing a clathrate compound comprising 1,1,2,2-tetrakis(4-hydroxyphenyl)ethane (hereinafter also referred to as TEP) and 2-phenyl-4-methyl-5-hydroxymethylimidazole (hereinafter also referred to as 2P4MHZ), crystals of the clathrate compound are obtained by suspending TEP and 2P4MHZ in ethyl acetate, heating the suspension under reflux for 3 hours, and then cooling the suspension to room temperature.

Further, a clathrate compound comprising at least an isophthalic acid compound and an imidazole compound is known, and Patent Document 2 describes that, as a method for producing the same, crystals of the clathrate compound are obtained by adding a methanol solution of 2-ethyl-4-methylimidazole (hereinafter also referred to as 2E4MZ) to a methanol solution of 5-nitroisophthalic acid (hereinafter also referred to as NIPA) with stirring under heating under reflux and then cooling the mixture overnight at room temperature after heating.

Patent Document 3 describes that, in an epoxy resin composition for sealing semiconductors which comprises an epoxy resin (A) and a clathrate complex (B) comprising 5-hydroxyisophthalic acid and 2-ethyl-4-methylimidazole, crystals of the clathrate complex are obtained by dropwise adding an ethyl acetate solution of 2E4MZ with heating to a mixture of 5-hydroxyisophthalic acid (hereinafter also referred to as HIPA) and ethyl acetate and then heating the resulting mixture under reflux for 2 hours.

PRIOR ART DOCUMENTS

Patent Documents

Patent Document 1: Japanese unexamined Patent Application Publication No. 2007-191450
Patent Document 2: International Publication No. WO 2008/075427
Patent Document 3: Japanese unexamined Patent Application Publication No. 2010-180337

SUMMARY OF THE INVENTION

Object to be Solved by the Invention

An object of the present invention is to provide a novel and industrially advantageous method for producing a clathrate compound which may obtain thermodynamically stable crystals of the clathrate compound at high purity.

Means to Solve the Object

As a result of extensive and intensive studies to achieve the above object, the present inventors have found that, by mixing a mixed solvent comprising a protic solvent, TEP or a specific isophthalic acid, and an imidazole compound followed by heating, a clathrate compound having thermodynamically more stable crystals is obtained as compared with a clathrate compound obtained by conventional production methods, and have completed the present invention.

Specifically, the present invention relates to:

(1) A method for producing a clathrate compound, comprising a mixing step of mixing the following component (A), component (B), and component (C); and a heating step, (A): a mixed solvent comprising a protic solvent, (B): at least one compound selected from the group consisting of 1,1,2,2-tetrakis(4-hydroxyphenyl)ethane, 5-hydroxyisophthalic acid, and 5-nitroisophthalic acid, (C): at least one compound selected from the group consisting of imidazole compounds represented by formula (I):

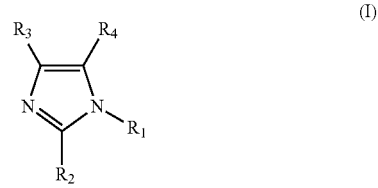

[wherein $R_1$ represents a hydrogen atom, a C1-C10 alkyl group, an aryl group, an aralkyl group, or a cyanoethyl group; and $R_2$ to $R_4$ represent a hydrogen atom, a nitro group, a halogen atom, a C1-C20 alkyl group, a C1-C20 alkyl group substituted with a hydroxyl group, an aryl group, an aralkyl group, or a C1-C20 acyl group];

(2) A method for producing a clathrate compound by crystal transformation comprising a mixing step of mixing the following component (A) and component (D); and a heating step, (A): a mixed solvent comprising a protic solvent, (D): a clathrate compound comprising at least one compound selected from the group consisting of 1,1,2,2-tetrakis(4-hydroxyphenyl)ethane, 5-hydroxyisophthalic acid, and 5-nitroisophthalic acid and at least one compound selected from the group consisting of imidazole compounds represented by formula (I):

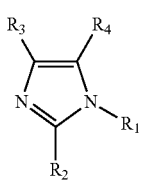

(I)

[wherein $R_1$ represents a hydrogen atom, a C1-C10 alkyl group, an aryl group, an aralkyl group, or a cyanoethyl group; and $R_2$ to $R_4$ represent a hydrogen atom, a nitro group, a halogen atom, a C1-C20 alkyl group, a C1-C20 alkyl group substituted with a hydroxyl group, an aryl group, an aralkyl group, or a C1-C20 acyl group];

(3) The method for producing a clathrate compound according to (1) or (2), wherein the mixed solvent comprises a first solvent which is at least one solvent selected from the group consisting of water and methanol and a second solvent which is at least one solvent selected from the group consisting of an alcoholic solvent, an ester-based solvent, a ketone-based solvent, an aliphatic hydrocarbon-based solvent, and an aromatic hydrocarbon-based solvent, the second solvent being a solvent different from the first solvent; and (4) The method for producing a clathrate compound according to (1) or (2), wherein the imidazole compound represented by formula (I) is 2-phenyl-4-methyl-5-hydroxymethylimidazole or 2-ethyl-4-methylimidazole.

EFFECT OF THE INVENTION

The production method according to the present invention is a method having a high industrial use value since a high-purity clathrate compound may be obtained even when a low-grade raw material is used. Since the clathrate compound obtained by the production method according to the present invention is in a crystal form which is more stable than clathrate compounds obtained by conventional production methods, it exhibits excellent curing characteristics when it is used as a curing agent or a curing accelerator for epoxy resin.

Mode for Carrying Out the Invention (Method for Producing Clathrate Compound According to the Present Invention)

The method for producing the clathrate compound according to the present invention is not particularly limited as long as it is a method comprising: a mixing step of mixing the following component (A), component (B), and a component (C); and a heating step, (A): a mixed solvent comprising a protic solvent, (B): at least one compound selected from the group consisting of 1,1,2,2-tetrakis(4-hydroxyphenyl)ethane, 5-hydroxyisophthalic acid, and 5-nitroisophthalic acid, and (C): at least one compound selected from the group consisting of imidazole compounds represented by formula (I).

Here, the clathrate compound is a compound constituted by two or more chemical species, each of which may be stably present alone. One of the chemical species builds a molecular-scale space and incorporates (includes) the other chemical species, where the prime requisite is that the shape and the size of the other chemical species match the space. Thereby, the clathrate compound has a specific crystal structure. The chemical species on the side of providing the space is referred to as a host, and the chemical species on the side of being included is referred to as a guest. The host and the guest are combined by interactions other than a covalent bond, such as a hydrogen bond, Van der Waals force, and an ionic bond. When the clathrate compound is an ionic bonding compound, it can be said that the clathrate compound forms an ionic crystal and a salt structure.

(Mixed Solvent Comprising Protic Solvent)

The component (A) of the present invention is not particularly limited as long as it is a mixed solvent in which at least one solvent is protonic, but it is preferably a mixed solvent comprising a first solvent and a second solvent.

Here, the first solvent is at least one solvent selected from the group consisting of water and methanol, and the second solvent is at least one solvent selected from the group consisting of an alcoholic solvent, an ester-based solvent, a ketone-based solvent, an aliphatic hydrocarbon-based solvent, and an aromatic hydrocarbon-based solvent.

As a specific example of the solvent used as the second solvent, an alcoholic solvent such as methanol and 2-propanol; an ester-based solvent such as ethyl acetate and butyl acetate; a ketone-based solvent such as methyl ethyl ketone and acetone; an aliphatic hydrocarbon-based solvent such as hexane, heptane, and cyclohexane; an aromatic hydrocarbon-based solvent such as benzene, toluene, and xylene or the like may be exemplified.

As a preferred combination of the first solvent and the second solvent, water and methanol, water and methyl ethyl ketone, methanol and methyl ethyl ketone, methanol and ethyl acetate, water and ethyl acetate, water and hexane or the like may be exemplified.

The first solvent and the second solvent are different solvents, and the combination and the percentage of the solvents may be arbitrarily selected in consideration of the solubility of a host compound and a guest compound in the solvents, the crystallinity of a clathrate compound to be produced, the miscibility of the solvents, and the like. However, when the first solvent is methanol, a solvent other than an alcohol solvent is preferably selected as the second solvent.

The ratio of the first solvent to the second solvent in the mixed solvent is not particularly limited, but the mass ratio of the first solvent/the second solvent at the start of the reaction is 1/99 to 99/1, preferably 2/98 to 80/20, and more preferably 2/98 to 70/30. In the present embodiment, the reaction is performed by using this mixed solvent under heating and stirring of the reaction mixture.

The amount of the mixed solvent used is different depending on the type and the percentage of the mixed solvent and is not particularly limited, but it is 0.5 to 50 parts by weight with respect to 1 part by weight of the component (B) and the component (C) in total or with respect to 1 part by weight of the component (D).

(Host Compound)

The host compound is at least one component (B) selected from the group consisting of 1,1,2,2-tetrakis(4-hydroxyphenyl)ethane, 5-hydroxyisophthalic acid, and 5-nitroisophthalic acid. When the compound of the component (B) is a compound having a carboxylic acid group, it forms a strong crystal structure as a clathrate compound since it provides a stronger hydrogen bond than a compound having a hydroxy group. Since the heat characteristics and the like of the resulting clathrate compound are different depending on the difference in the host compound, the host compound may be arbitrarily selected depending on the use mode.

(Guest Compound)

The guest compound is at least one component (C) selected from the group consisting of imidazole compounds represented by formula (I):

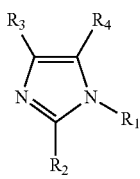

[wherein $R_1$ represents a hydrogen atom, a C1-C10 alkyl group, an aryl group, an aralkyl group, or a cyanoethyl group; and $R_2$ to $R_4$ represent a hydrogen atom, a nitro group, a halogen atom, a C1-C20 alkyl group, a C1-C20 alkyl group substituted with a hydroxyl group, an aryl group, an aralkyl group, or a C1-C20 acyl group].

As the C1-C10 alkyl group of $R_1$, a methyl group, an ethyl group, a propyl group, an isopropyl group, a cyclopropyl group, a butyl group, an isobutyl group, a s-butyl group, a t-butyl group, a cyclobutyl group, a cyclopropylmethyl group, a pentyl group, an isopentyl group, a 2-methylbutyl group, a neopentyl group, a 1-ethylpropyl group, a hexyl group, an isohexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 1-ethylbutyl group, a 2-ethylbutyl group, an octyl group, a nonyl group, a decyl group or the like may be exemplified.

As the C1-C20 alkyl group of $R_2$ to $R_4$, an undecyl group, a lauryl group, a palmityl group, a stearyl group or the like may be exemplified in addition to those listed as the alkyl group of $R_1$.

As the C1-C20 alkyl group substituted with a hydroxyl group of $R_2$ to $R_4$, a hydroxymethyl group, a hydroxyethyl group or the like may be exemplified.

As the C1-C20 acyl group of $R_2$ to $R_4$, a formyl group; an alkyl-substituted acyl group such as an acetyl group, a propionyl group, a butyryl group, an isobutyryl group, a valeryl group, an isovaleryl group, a pivaloyl group, a hexanoyl group, an octanoyl group, a decanoyl group, a lauroyl group, a myristoyl group, a palmitoyl group, and a stearoyl group; an alkenyl-substituted acyl group such as an acryloyl group and a methacryloyl group; an aryl-substituted acyl group such as a benzoyl group, a toluoyl group, and a naphthoyl group; a cycloalkyl-substituted acyl group such as a cyclohexylcarbonyl group; an acyl group having a halogen atom such as a chloroformyl group; or the like may be exemplified.

The aryl group of $R_2$ to $R_4$ relates to a monocyclic or polycyclic aryl group. Here, in the case of a polycyclic aryl group, the aryl group also includes a partially saturated group in addition to a fully unsaturated group. For example, a C6-10 aryl group such as a phenyl group, a naphthyl group, an azulenyl group, an indenyl group, an indanyl group or a tetranyl group may be exemplified.

As the aralkyl group of $R_2$ to $R_4$, which is a group in which the aryl group and the alkyl group are combined, a C6-10 aryl C1-6 alkyl group such as a benzyl group, a phenethyl group, a 3-phenyl-n-propyl group, a 1-phenyl-n-hexyl group, a naphthalene-1-ylmethyl group, a naphthalene-2-ylethyl group, a 1-naphthalene-2-yl-n-propyl group or an indene-1-ylmethyl group may be exemplified.

As the halogen atom, a fluorine atom, a chlorine atom, a bromine atom or an iodine atom may be exemplified.

The alkyl group, the aryl group, the aralkyl group, and the acyl group of $R_1$ to $R_4$ are optionally substituted, and as the substituent, an alkyl group, a hydroxy group, an alkoxy group, an aryl group, an aralkyl group or a halogen atom may be exemplified.

As specific examples of these groups as a substituent, the same groups as those described above may be exemplified. Note that as specific examples of the alkyl group part of the alkoxy group, the same as the above alkyl groups may be exemplified.

As a specific example of the imidazole compound, imidazole, 1-methylimidazole, 2-methylimidazole, 3-methylimidazole, 4-methylimidazole, 5-methylimidazole, 1-ethylimidazole, 2-ethylimidazole, 3-ethylimidazole, 4-ethylimidazole, 5-ethylimidazole, 1-n-propylimidazole, 2-n-propylimidazole, 1-isopropylimidazole, 2-isopropylimidazole, 1-n-butylimidazole, 2-n-butylimidazole, 1-isobutylimidazole, 2-isobutylimidazole, 2-undecyl-1H-imidazole, 2-heptadecyl-1H-imidazole, 1,2-dimethylimidazole, 1,3-dimethylimidazole, 2,4-dimethylimidazole, 2-ethyl-4-methylimidazole, 1-phenylimidazole, 2-phenyl-1H-imidazole, 4-methyl-2-phenyl-1H-imidazole, 2-phenyl-4-methylimidazole, 1-benzyl-2-methylimidazole, 1-benzyl-2-phenylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole, 2-phenyl-4,5-dihydroxymethylimidazole, 2-phenyl-4-methyl-5-hydroxymethylimidazole, 1-cyanoethyl-2-phenyl-4,5-di(2-cyanoethoxy)methylimidazole or the like may be exemplified.

Among them, at least one imidazole compound selected from the group consisting of 2-ethyl-4-methylimidazole and 2-phenyl-4-methyl-5-hydroxymethylimidazole is more preferred.

(Mixing Step)

The mixing step of the present invention is not particularly limited as long as it accomplishes the mixing of a mixed solvent described in the component (A), a compound described in the component (B) (hereinafter also referred to as a host compound), and a compound described in the component (C) (hereinafter also referred to as a guest compound), and examples include the following methods:

(a) A host compound and a guest compound are added to a mixed solvent.
(b) A host compound is added to a mixed solvent, and then a guest compound is added thereto.
(c) A guest compound is added to a mixed solvent, and then a host compound is added thereto.
(d) A host compound is added to a mixed solvent, and then a guest compound dissolved in a solvent is added thereto. (However, the solvent used for dissolving the guest compound is preferably the same as at least one of the solvent components constituting the mixed solvent.)
(e) A host compound is added to a mixed solvent, and then a heat-melted guest compound is added thereto (in the case where the guest compound is a solid).
(f) A host compound is mixed with a mixed solvent, and then a guest compound is added to the mixture while heating the mixture.
(g) A host compound dissolved in a mixed solvent is added to a guest compound.

A host compound and a guest compound are dissolved or suspended in a mixed solvent, but the both compounds are preferably dissolved in the solvent. When these compounds are dissolved in the solvent, the whole amount thereof is not necessarily dissolved in the solvent, but at least a very small part thereof may be dissolved in the solvent. Further, when a guest compound is a solid, the guest compound may be mixed with a guest compound and/or a mixed solvent after melting the guest compound.

The mixing ratio of a guest compound to a host compound in the production of a clathrate compound is preferably 0.1 to 10 mol, and more preferably 0.5 to 5.0 mol, of the guest compound with respect to 1 mol of the host compound.

(Heating Step)

The heating step of the present invention is not particularly limited as long as it comprises a step of performing heat treatment somewhere in the production process, but the heat treatment is preferably performed during the mixing step and/or after the mixing step.

The heating temperature is different according to the type of a solvent to be used, but it is, for example, in the range of 40 to 150° C. and is preferably achieved by heating under reflux. The heating time is 5 minutes to 12 hours, and preferably 1 to 3 hours.

(Other Steps)

The method for producing a clathrate compound according to the present invention may have other steps before and after any of the mixing step or the heating step, as long as the effects of the present invention are not deteriorated. As an example of other steps, a step of cooling a mixture after the heating step;
a step of filtering the cooled mixture;
a step of drying the material obtained by filtering to obtain crystals of a clathrate compound;
a step of grinding a host compound and a guest compound before the mixing step when the host compound and the guest compound are solids;
or the like may be exemplified.

Here, the particle size of a host compound or a guest compound is not particularly limited as long as the effects of the present invention are obtained, but the average particle size is preferably 50 μm or less, and more preferably 20 μm or less.

(Clathrate Compound)

The proportion of a host compound and a guest compound comprised in a clathrate compound is not particularly limited as long as the host compound and the guest compound may form the clathrate compound, but the guest compound is preferably 0.1 to 10 mol, and more preferably 0.5 to 5.0 mol, with respect to 1 mol of the host compound.

When a clathrate compound comprises a third component, the third component is preferably 40 mol % or less, and more preferably 10% or less, with respect to the whole amount of the clathrate compound, and particularly preferably, the clathrate compound does not comprise the third component. Further, a multicomponent clathrate compound consisting of three or more components may also be obtained by allowing two or more guest compounds to react with a host compound.

(Method for Producing Clathrate Compound by Crystal Transformation)

The present invention also comprises a method of obtaining a clathrate compound which is the same as that obtained by the method described above by subjecting the clathrate compound obtained by a known production method to crystal transformation.

The method for producing a clathrate compound in this case is not particularly limited, as long as it is a method comprising a mixing step of mixing a component (A) and a component (D), and a heating step, (A): a mixed solvent comprising a protic solvent,
(D): a clathrate compound comprising at least one selected from the group consisting of 1,1,2,2-tetrakis(4-hydroxyphenyl)ethane, 5-hydroxyisophthalic acid, and 5-nitroisophthalic acid and at least one selected from the group consisting of imidazole compounds represented by formula (I):

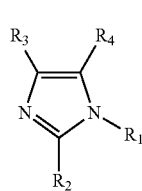

[wherein $R_1$ represents a hydrogen atom, a C1-C10 alkyl group, an aryl group, an aralkyl group, or a cyanoethyl group; and $R_2$ to $R_4$ represent a hydrogen atom, a nitro group, a halogen atom, a C1-C20 alkyl group, a C1-C20 alkyl group substituted with a hydroxyl group, an aryl group, an aralkyl group, or a C1-C20 acyl group].

The component (A) is as described above.

The clathrate compound described in the component (D) may be produced using a known method. For example, a method of obtaining a clathrate compound in which a host compound and a guest compound are added to a solvent, the resulting mixture is then subjected to heat treatment or heating-under-reflux treatment optionally with stirring, and the clathrate compound is then precipitated; a crystallization method in which the host compound and the guest compound are once dissolved in a solvent, and the solvent is then cooled to precipitate crystals; or the like may be exemplified, but the known method is not limited to these methods. Note that the imidazole compound comprised in the component (D) is as described above.

The mixing step and the heating step may be performed in the same manner as in the mixing step and the heating step described above.

The clathrate compound produced by the method according to the present invention may be suitably used for the applications of curing an epoxy resin, for example, for the applications such as an epoxy resin adhesive, a semiconductor sealing material, a laminate sheet for a printed wiring board, varnish, a powder coating material, ink, and a fiber-reinforced composite material.

EXAMPLES

Hereinafter, the present invention will be explained in detail below referring to Examples, but the present invention is not intended to be limited to the Examples.

Example 1 to Example 8

To a flask, were added TEP (product name: TEP-DF, manufactured by ASAHI YUKIZAI CORPORATION), 2P4MHZ (product name: 2P4MHZ-PW, manufactured by Shikoku Chemicals Corporation), and a mixed solvent in amounts shown in Table 1, and the mixture was heated under reflux for 3 hours with stirring. The resulting mixture was cooled, filtered, and dried to obtain a clathrate compound (crystal B) having an clathrate ratio (TEP:2P4MHZ)=1:2.

The clathrate compound obtained in Example 1 was subjected to thermogravimetry-differential scanning calorimetry (TG-DSC). The TG-DSC measurement was performed using a thermogravimetry apparatus (product name: TGA-DSC1, manufactured by Mettler-Toledo International Inc.) and installing about 3 mg of the crystal in an aluminum container, and the measurement was performed under a nitrogen purge (at a flow rate of 50 mL/min) at a temperature increase rate of 20° C./min in a temperature range of 30 to 500° C. As a result, the 2P4MHZ release temperature of the resulting clathrate compound was 231° C. The same measurement results were obtained also in Examples 2 to 8.

TABLE 1

|  |  | Example 1 | Example 2 | Example 3 | Example 4 | Example 5 | Example 6 | Example 7 | Example 8 |
|---|---|---|---|---|---|---|---|---|---|
| | TEP (Upper row: g, Lower row: mmol) | 19.8 (49.7) | 4.95 (12.4) | 4.95 (12.4) | 4.95 (12.4) | 4.95 (12.4) | 4.95 (12.4) | 19.8 (49.7) | 49.5 (124) |
| | 2P4MHZ (Upper row: g, Lower row: mmol) | 17.8 (94.6) | 4.45 (23.6) | 4.45 (23.6) | 4.45 (23.6) | 4.45 (23.6) | 4.45 (23.6) | 17.8 (94.6) | 44.5 (236) |
| Mixed solvent | Ethyl acetate (ml) | 200 | 50 | 0 | 0 | 0 | 0 | 200 | 0 |
| | Hexane (ml) | 0 | 0 | 50 | 50 | 0 | 0 | 0 | 0 |
| | Water (ml) | 20 | 0 | 5 | 0 | 15 | 35 | 6 | 200 |
| | Methanol (ml) | 0 | 5 | 0 | 15 | 35 | 15 | 0 | 200 |
| | The resulting amount of clathrate compound (crystal B) (g) | 35.2 | 8.97 | 8.95 | 8.87 | 8.62 | 9.05 | 35.8 | 90.7 |
| | Recovery rate (%) | 96 | 98 | 98 | 97 | 94 | 99 | 98 | 99 |

Comparative Example 1

A clathrate compound of TEP and 2P4MHZ was produced in accordance with the method described in Patent Document 1 to obtain a clathrate compound (crystal A).

TG-DSC measurement of the resulting clathrate compound was performed using the same apparatus and under the same conditions as in Example 1. As a result, the 2P4MHZ release temperature of the resulting clathrate compound was 223° C. It was found that the crystal B had higher release temperature than the crystal A, and that the crystal B was in a thermodynamically more stable crystal form.

Example 9 to Example 11

To a flask, were added a clathrate compound (crystal A) and a mixed solvent each in an amount shown in Table 2, and the mixture was heated under reflux for 3 hours with stirring. The resulting mixture was cooled, filtered, and dried to obtain a clathrate compound (crystal B). TG-DSC measurement of each clathrate compound was performed, and the same results as in Example 1 were obtained.

TABLE 2

|  | Example 9 | Example 10 | Example 11 |
|---|---|---|---|
| Clathrate compound obtained in Comparative Example 1 (crystal A) (Upper row: g, Lower row: mmol) | 20.0 (25.8) | 10.0 (12.9) | 10.0 (12.9) |
| Mixed solvent Ethyl acetate (ml) | 100 | 50 | 0 |
| Water (ml) | 10 | 0 | 40 |
| Methanol (ml) | 0 | 25 | 40 |
| The resulting amount of clathrate compound (crystal B) (g) | 18.6 | 7.90 | 9.38 |
| Recovery rate (%) | 93 | 79 | 94 |

Example 12 to Example 16

To a flask, were added 3.04 g (16.7 mmol) of HIPA and a mixed solvent in an amount described in Table 3, and the mixture was stirred. Thereto, was dropwise added 1.84 g (16.7 mmol) of 2E4MZ (product name: 2E4MZ, manufactured by Shikoku Chemicals Corporation) which was previously dissolved in ethyl acetate or methyl ethyl ketone, and the mixture was then heated under reflux for 3 hours with stirring. The resulting mixture was cooled, filtered, and dried to obtain a clathrate compound (crystal D) having an clathrate ratio (HIPA:2E4MZ)=1:1.

TG-DSC measurement of the clathrate compound obtained in Example 12 was performed using the same apparatus and under the same conditions as in Example 1. As a result, the 2E4MZ release temperature of the resulting clathrate compound was 189° C. The same measurement results were obtained also in Examples 13 to 16.

TABLE 3

|  |  | Example 12 | Example 13 | Example 14 | Example 15 | Example 16 |
|---|---|---|---|---|---|---|
| | HIPA (Upper row: g, Lower row: mmol) | 3.04 (16.7) | 3.04 (16.7) | 3.04 (16.7) | 3.04 (16.7) | 3.04 (16.7) |
| | 2E4MZ (Upper row: g, Lower row: mmol) | 1.84 (16.7) | 1.84 (16.7) | 1.84 (16.7) | 1.84 (16.7) | 1.84 (16.7) |
| Mixed solvent | Ethyl acetate (ml) | 50 | 50 | 50 | 0 | 0 |
| | MEK (ml)* | 0 | 0 | 0 | 50 | 50 |
| | Water (ml) | 0 | 5 | 1 | 0 | 1 |
| | Methanol (ml) | 5 | 0 | 0 | 5 | 0 |
| | The resulting amount of clathrate compound (crystal D) (g) | 3.99 | 3.57 | 3.84 | 3.91 | 4.50 |
| | Recovery rate (%) | 82 | 73 | 79 | 80 | 92 |

*In the table, MEK represents methyl ethyl ketone.

Comparative Example 2

A clathrate compound of HIPA and 2E4MZ was produced in accordance with the method described in Patent Document 3 to obtain a clathrate compound (crystal C).

TG-DSC measurement of the resulting clathrate compound was performed using the same apparatus and under the same conditions as in Example 1. As a result, the 2E4MZ release temperature of the resulting clathrate compound was 173° C. It was found that the crystal D had higher release temperature than the crystal C, and that the crystal D was in a thermodynamically more stable crystal form.

Example 17 to Example 23

To a flask, were added a clathrate compound (crystal C) and a mixed solvent each in an amount shown in Table 4, and the mixture was heated under reflux for 3 hours with stirring. The resulting mixture was cooled, filtered, and dried to obtain a clathrate compound (crystal D). TG-DSC measurement of each clathrate compound was performed, and the same results as in Example 12 were obtained.

TABLE 4

|  |  | Example 17 | Example 18 | Example 19 | Example 20 | Example 21 | Example 22 | Example 23 |
|---|---|---|---|---|---|---|---|---|
| Clathrate compound obtained in Comparative Example 2 (crystal C) (Upper row: g, Lower row: mmol) | | 5.0 (17.1) | 5.0 (17.1) | 5.0 (17.1) | 5.0 (17.1) | 5.0 (17.1) | 5.0 (17.1) | 30.0 (103) |
| Mixed solvent (ml) | Ethyl acetate | 50 | 0 | 50 | 50 | 0 | 0 | 0 |
| | MEK (ml)* | 0 | 50 | 0 | 0 | 50 | 50 | 0 |
| | Water (ml) | 1 | 1 | 0 | 0 | 0 | 0 | 20 |
| | Methanol (ml) | 0 | 0 | 1 | 5 | 1 | 5 | 20 |
| The resulting amount of clathrate compound (crystal D) (g) | | 4.96 | 4.83 | 4.77 | 4.75 | 4.73 | 4.78 | 23.0 |
| Recovery rate (%) | | 99 | 97 | 95 | 95 | 95 | 96 | 77 |

In the table, MEK represents methyl ethyl ketone.

Example 24

A low-grade TEP comprising a large amount of sodium component, 2P4MHZ, and a mixed solvent were mixed each in an amount shown in Table 5, and the mixture was heated under reflux for 3 hours with stirring. The resulting mixture was cooled, filtered, and dried to obtain a clathrate compound.

Table 5 shows the results of measuring the concentration of sodium element comprised in each component using ICP-AES (inductively coupled plasma-atomic emission spectroscope). These results show that since the sodium element comprised in the low-grade TEP is eluted into filtrate after filtration and does not remain in the resulting clathrate compound, a high-purity clathrate compound may be obtained by using the production method of the present invention even when low-grade raw material is used.

TABLE 5

| | Mixed amount of each component | Concentration of sodium element comprised in each component (ppm) |
|---|---|---|
| Low-grade TEP | 49.7 g (0.12 mol) | 3.2 |
| 2P4MHZ | 44.7 g (0.24 mol) | Below quantitation limit |
| Mixed Water | 200 ml | Below quantitation limit |
| solvent Methanol | 159 ml | Below quantitation limit |
| Clathrate compound (crystal B) | 93.5 g | Below quantitation limit |
| Filtrate | 256 g | 0.83 |

The invention claimed is:

1. A method for producing a thermodynamically stable crystal of a clathrate compound, comprising a mixing step of mixing the following component (A), component (B), and component (C); and a heating step:

(A): a mixed solvent comprising a first solvent which is at least one solvent selected from the group consisting of water and methanol; and a second solvent which is at least one solvent selected from the group consisting of ethyl acetate, hexane, methyl ethyl ketone, and methanol, the second solvent being a solvent different from the first solvent, (B): at least one compound selected from the group consisting of 1,1,2,2-tetrakis(4-hydroxyphenyl)ethane and 5-hydroxyisophthalic acid, (C): at least one compound selected from the group consisting of 2-phenyl-4-methyl-5-hydroxymethylimidazole and 2-ethyl-4-methylimidazole.

2. A method for producing a thermodynamically stable crystal of a clathrate compound which is different from (D) by crystal transformation comprising a mixing step of mixing the following component (A) and component (D); and a heating step:

(A): a mixed solvent comprising a first solvent which is at least one solvent selected from the group consisting of water and methanol; and a second solvent which is at least one solvent selected from the group consisting of ethyl acetate, hexane, methyl ethyl ketone, and methanol, the second solvent being a solvent different from the first solvent, (D): a clathrate compound comprising at least one compound selected from the group consisting of 1,1,2,2-tetrakis(4-hydroxyphenyl)ethane, and 5-hydroxyisophthalic acid and at least one compound selected from the group consisting of 2-phenyl-4-methyl-5-hydroxymethylimidazole and 2-ethyl-4-methylimidazole.

* * * * *